United States Patent [19]

Kaieda et al.

[11] Patent Number: 4,572,805

[45] Date of Patent: Feb. 25, 1986

[54] 2,3,5,6-TETRAFLUOROPHENYL (METH) ACRYLATES AND METHOD FOR PRODUCTION THEREOF

[75] Inventors: Osamu Kaieda, Mishima; Koichi Hirota, Suita; Isao Okitaka; Toshiaki Nakamura, both of Osaka, all of Japan

[73] Assignee: Nippon Shokubai Kagaku Kogyo Co., Ltd., Osaka, Japan

[21] Appl. No.: 708,289

[22] Filed: Mar. 5, 1985

[30] Foreign Application Priority Data

Mar. 27, 1984 [JP] Japan .................................. 59-57354
Mar. 29, 1984 [JP] Japan .................................. 59-59348

[51] Int. Cl.$^4$ ............................................ C07C 121/50
[52] U.S. Cl. .................................. 260/465 D; 560/130
[58] Field of Search .................... 560/130; 260/465 D

[56] References Cited

PUBLICATIONS

Luigi Magagnini et al., Gazz. Chim. Ital., 96, 1035 (1966).

Gene Sumrell et al., J. Amer. Chem. Soc., 81, 4310 (1959).

Allen R. Banks, J. Org. Chem., 42, 3965 (1977).

*Primary Examiner*—Paul R. Michl
*Assistant Examiner*—Alex H. Walker
*Attorney, Agent, or Firm*—Omri M. Behr

[57] ABSTRACT

2,3,5,6-Tetrafluorophenyl (meth)acrylates represented by the general formula I:

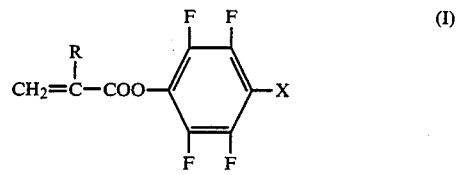

wherein R is H or CH$_3$ and X is H or CN are disclosed. These compounds are obtained by the reaction of 4-cyano-substituted or unsubstituted 2,3,5,6-tetrafluorophenols with (meth)acrylic acid chloride.

13 Claims, No Drawings

2,3,5,6-TETRAFLUOROPHENYL (METH) ACRYLATES AND METHOD FOR PRODUCTION THEREOF

BACKGROUND OF THE INVENTION

Field of the Invention

This invention relates to 2,3,5,6-tetrafluorophenyl (meth)acrylates and to a method for the production thereof.

SUMMARY OF THE INVENTION

The objects described above are accomplished by compounds represented by the general formula I:

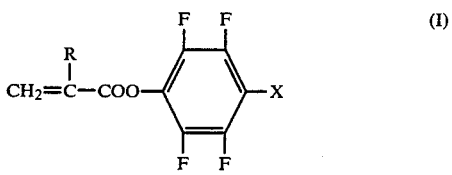

wherein R denotes hyrogen atom or methyl group and x denotes hydrogen atom or cyano group.

These objects are also accomplished by a method for the production of compounds represented by the general formula I, which comprises causing (meth)acrylic acid chlorides to react with 2,3,5,6-tetrafluorophenols represented by the general formula II:

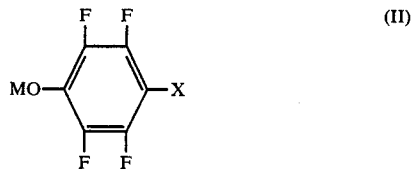

wherein M denotes hydrogen atom or an alkali metal atom and X has the same meaning as described above.

EXPLANATION OF PREFERRED EMBODIMENT the 2,3,5,6-tetrafluorophenyl (meth)acrylates, which are the compound of this invention represented by the general formula I, are produced by the reaction of 2,3,5,6-tetrafluorophenols represented by the general formula II with acrylic acid chloride or methacrylic acid chloride.

For example, 2,3,5,6-tetrafluorophenyl acrylate is obtained by the reaction of 2,3,5,6-tetrafluorophenol or an alkali metal salt thereof with acrylic acid chloride, 2,3,5,6-tetrafluorophenyl methacrylate by the reaction of 2,3,5,6-tetrafluorophenol or an alkali metal salt thereof with methacrylic acid chloride, 4-cyano-2,3,5,6-tetrafluorophenyl acrylate by the reaction of 4-cyano-2,3,5,6-tetrafluorophenol or an alkali metal salt thereof with acrylic acid chloride, and 4-cyano-2,3,5,6-tetrafluorophenyl methacrylate by the reaction of 4-cyano-2,3,5,6-tetrafluorophenol or an alkali metal salt thereof with methacrylic acid chloride. The term "alkali metal salt" as used in this specification embraces lithium salts, sodium salts, potassium salts, for example. Among other alkali metal salts, sodium salts, etc. are used preferably herein.

The amount of (meth)acrylic acid chloride to be used in the reaction per mol of 2,3,5,6-tetrafluorophenols is in the range of 1.0 to 2.0 mols, preferably 1.05 to 1.6 mols.

The aforementioned reaction is generally carried out in an organic solvent. Typical exmaples of the organic solvent usable therefor include methanol, ethanol, isopropanol, butanols, benzene, toluene, xylenes, carbon tetrachloride, perchloroethylene, etc. In this case, the concentration of the 2,3,5,6-tetrafluorophenols in the organic solvent is generally in the range of 2 to 30% by weight, preferably 3 to 20% by weight. The reaction system is desired to have a hydrogen chloride trapping agent contained therein. Typical examples of the hydrogen chloride trapping agent include lithium hydroxide, sodium hydroxide, potassium hydroxide, magnesium carbonate, triethylamine, pyridine, molecular sieve, etc. The amount of this hydrogen chloride trapping agent so contained in the reaction system is desired to exceed the theoretical amount enough to react all the hydrogen chloride by-produced in the reaction.

The reaction temperature is in the range of $-20°$ to $+120°$ C., preferably $-5°$ to $+90°$ C. The reaction time is in the range of 0.5 to 100 hours, preferably 1 to 70 hours.

The 2,3,5,6-tetrafluorophenyl (meth)acrylates of this invention represented by the general formula I excel in the polymerizing property and, theerefore, are usable as raw materials for homopolymers or copolymers. They can be converted into various useful fluorine-containing (meth)acrylate polymers. These fluorine-containing (meth)acrylate polymers possess special functions dissimilar to the functions of the ordinary (meth)acrylate polymers containing no fluorine. These (meth)acrylate polymers, excelling in resistance to heat, resistance to light, and flame retardance, find utility in applications to plastics, coating materials, and adhesive agents. They are also usable as monomers for the production of electron beam resists, optical fiber sheaths, and organic photosensitive binders.

Now, the method for the production of novel substances of the present invention will be described specifically below with reference to working examples. The analyses obtained of the novel substances so produced for the determination of their chemical structures are shown at the same time.

EXAMPLE 1

Synthesis of 4-cyano-2,3,5,6-tetrafluorophenol

A three-neck flask was charged with 250 g (1.295 mols) of pentafluorobenzonitrile, 171 g (3.05 mols) of potassium hydroxide and 500 ml of 2-methyl-2-propanol as a solvent. In an atmosphere of nitrogen gas, the contents of the flask were held as stirred at 70° C. for 20 hours for reaction. Then, the reaction mixture was evaporated to dryness to expel 2-methyl-2-propanol. The residue of the flask was dissolved in 250 ml of water.

The resultant aqueous solution was adjusted to pH 2 by dropwise addition thereof of 6N sulfuric acid. It was added to 500 ml of ether to effect extraction of the organic substance. This extraction was repeated twice. The ether layer was dried with magnesium sulfate and then evaporated to drynes to expel ether. The residual crystals were recrystallized from benzene to obtain 4-cyano-2,3,5,6-tetrafluorophenol (yeild 81.3 mol % based on pentafluorobenzonitrile).

m.p. 128°–129° C.

$^{19}F$ NMR (solvent: acetone-$d_6$, external standard substance: trifluoroacetic acid)

δ=61.4 ppm (doublet-multiplet, 2F)
δ=84.7 ppm (doublet-multiplet, 2F)

EXAMPLE 2

In 200 ml of carbon tetrachloride, 19.1 g (0.100 mol) of 4-cyano-2,3,5,6-tetrafluorophenol and 13.0 g (0.125 mol) of methacrylic acid chloride were dissolved. To the resultant solution was added 20 g of molecular sieve 3 Å in diameter. The resultant mixture was refluxed as agitated for 48 hours. The reaction mixture so produced was cooled and then filtered to separate the molecular sieve. The filtrate was dried with magnesium sulfate and then evaporated to dryness with a rotary evaporator. Consequently, there was obtained 21.7 g of 4-cyano-2,3,5,6-tetrafluorophenyl methacrylate (yield 83.8% based on 4-cyano-2,3,5,6-tetrafluorophenol, purity 96.5%).

The analyses obtained of this novel substance for the determination of its chemical structure are shown below.

4-Cyano-2,3,5,6-tetrafluorophenyl methacrylate recrystallized with benzene

Melting point 87°–88° C.
Elementary analyses

|  | C (%) | H (%) | F (%) | N (%) |
|---|---|---|---|---|
| Calculated | 50.97 | 1.93 | 29.34 | 5.41 |
| Found | 50.8 | 1.98 | 29.1 | 5.44 |

$^1$H NMR (solvent: CCl$_4$, internal standard substance: TMS)

| CH$_3$ | δ = 2.1 ppm (Singlet, 3H) |
|---|---|
| CH$_2$ | δ = 5.9 ppm (Singlet, 1H) |
|  | δ = 6.4 ppm (Singlet, 1H) |

$^{19}$F NMR (solvent: acetone-d$_6$, external standard substance: trifluoroacetic acid)
δ=58.8 ppm (doublet-doublet, $^J$AB, A'B'≈21 Hz, $^J$AB', A'B≈10 Hz, 2F)
δ=75.3 ppm (doublet-doublet, $^J$BA, B'A'≈21 Hz, $^J$BA', B'A≈10 Hz, 2F)
Mass analysis spectrum EI m/e=259 (M+)
Infrared absorption spectrum (KBr) 2250 cm$^{-1}$ ($^v$C≡N);
1760 cm$^{-1}$ ($^v$C=O);
1650 cm$^{-1}$ ($^v$C=C);
1500 cm$^{-1}$ ($^v$F—benzene ring C=C).

EXAMPLE 3

In 50 ml of methanol having 0.94 g (0.0236 mol) of sodium hydroide dissolved therein, 3.0 g (0.0157 mol) of 4-cyano-2,3,5,6-tetrafluorophenol was dissolved. The resultant solution was kept with ice at 0° C. To the cooled solution, 1.80 g (0.0173 mol) of methacrylic acid chloride as slowly added dropwise. After completion of this dropwise addition, the resultant mixture was stirred at the same temperature for two hours. It was then mixed with 50 ml of pure water and adjusted to pH 10 by addition of an aqueous 20% sodium hydroide solution. As the result, white crystals occurred. The white crystals were filtered, washed with cold water, and then dried to obtain 1.35 g of 4-cyano-2,3,5,6-tetrafluorophenyl methacrylate (purity 98% and yield 32 mol % based on 4-cyano-2,3,5,6-tetrafluorophenol). The analyses obtained of this novel substance for the determination of its chemical structure were the same as those of Example 2.

EXAMPLE 4

In 30 ml of benzene, 3.0 g (0.0157 mol) of 4-cyano-2,3,5,6-tetrafluorophenol and 1.80 g (0.0173 mol) of methacrylic acid chloride were dissolved. The resultant solution, and 1.73 g (0.0173 mol) of calcium carbonate added thereto as a hydrogen chloride trapping agent were stirred under reflux for 32 hours. The resultant reaction mixture was cooled off and filtered to separate calcium carbonate. The filtrate was dried with magnesium sulfate and then evaporated with a rotary evaporator. Consequently, there was obtained 2.6 g of 4-cyano-2,3,5,6-tetrafluorophenyl methacrylate (yeild 63.9% and purity 95.4%). The analyses obtained of the novel substance for the determination of its chemical structure were the same as those of Example 2.

EXAMPLE 5

In 200 ml of carbon tetrachloride, 19.1 g (0.100 mol) of 4-cyano-2,3, 5,6-tetrafluorophenol and 11.3 g (0.125 mol) of acrylic acid chloride were dissolved. To the resultant solution, 20 g of molecular sieve 3 Å in diameter was added. The mixture was stirred under reflux for 38 hours. The resultant reaction mixture was cooled off and filtered to separate the molecular sieve. The filtrate was dried with magnesium sulfate and evaporated to dryness with a rotary evaporator. Consequently, there was obtained 15.2 g of 4-cyano-2,3,5,6-tetrafluorophenyl acrylate (yield 62.0% based on 4-cyano-2,3,5,6-tetrafluorophenol, purity 96.4%) having a melting point below determined.

The analyses obtained of this novel substance for the determination of its chemical structure are shown below.

Boiling point 62° C. (2 mmHg)
Melting point 21°–23° C.
Elementary analyses

|  | C (%) | H (%) | F (%) | N (%) |
|---|---|---|---|---|
| Calculated | 48.98 | 1.22 | 31.02 | 5.71 |
| Found | 48.9 | 1.25 | 30.8 | 5.77 |

$^1$H NMR (solvent: CCl$_4$, internal standard substance: TMS)
δ=5.9–7.0 ppm (multiplet, 3H)
$^{19}$F NMR (solvent: acetone-d$_6$, external standard substance: trifluoroacetic acid)
δ=58.7 ppm (broad doublet, J=21 Hz, 2F)
δ=75.2 ppm (broad doublet, J=21 Hz, 2 F)
Mass analysis spectrum EI m/e=245 (M+)
Infrared absorption spectrum (neat) 2250 cm$^{-1}$ ($^v$C≡N) 1770 cm$^{-1}$ ($^v$C=O) 1630 cm$^{-1}$ ($^v$C=C) 1500 cm$^{-1}$ ($^v$F—benzene ring C=C)

EXAMPLE 6

In 30 ml of benzene, 3.82 g (0.020 mol) of 4-cyano-2,3,5,6-tetrafluorophenol and 2.26 g (0.025 mol) of calcium carbonate added thereto as a hydrogen chloride trapping agent were stirred under reflux for 40 hours. The resultant reaction mixture was cooled off and filtered to separate calcium carbonate. The filtrate was dried with magnesium sulfate and then evaporated to dryness with a rotary evaporator. Consequently, there was obtained 2.8 g of 4-cyano-2,3, 5,6-tetrafluorophenyl acrylate (yield 57.1%, purity 95.8%). The analyses obtained of the novel substance for the determination of its chemical structure were the same as those of Example 5.

EXAMPLE 7

In 200 ml of methanol having 4.32 g (0.108 mols) of sodium hydroxide dissolved therein, 12 g (0.0723 mol) of 2,3,5,6-tetrafluorophenol was dissolved. The resultant solution was kept at 0° C. with ice. To the cooled solution, 8.32 g (0.0796 mol) of methacrylic acid chloride was slowly added dropwise. After completion of the dropwise addition, the mixture was stirred at the same temperature for 1.5 hours. The mixture was combined with 160 ml of pure water and adjusted to pH 10 by addition of an aqueous 20% sodium hydroxide solution. Consequently, the reaction mixture separated into two layers. Of the two layers, the oil layer was separated, washed again with pure water, dried with anhydrous sodium sulfate, and then rectified with a precision fractionator to recover 12.1 g of 2,3,5,6-tetrafluorophenyl methacrylate, as a fraction boiling at 56° to 57° C./3.5 mmHg, (yield 71.5 mol % based on 2,3,5,6-tetrafluorophenol).

The analyses obtained of the novel substance for the determination of its chemical structure are shown below.

Boiling point 56°–57° C. (3.5 mmHg)
Elementary analyses

|  | C (%) | H (%) | F (%) |
| --- | --- | --- | --- |
| Calculated | 51.28 | 2.59 | 32.45 |
| Found | 51.3 | 2.56 | 32.3 |

$^1$H NMR (solvent: CCl$_4$, internal standard substance: TMS)

$\delta = 2.08$ ppm (singlet, 3H)
$\delta = 5.80$ ppm (singlet, 1H)
$\delta = 6.35$ ppm (singlet, 1H)
$\delta = 6.95$ ppm (quintet, J$_{HF}$=9 Hz, 1H)

$^{19}$F NMR (solvent: acetone—d$_6$, external standard substance: trifluoroacetic acid)

$\delta = 64.4$ ppm (broad singlet, 2F)
$\delta = 78.6$ ppm (broad singlet, 2F)

Mass analysis spectrum EI m/e=234 (M+)
Infrared absorption spectrum (neat) 1760 cm$^{-1}$ ($\nu$C=O); 1640 cm$^{-1}$ ($\delta$C=C); 1490, 1530 cm$^{-1}$ ($\nu$F— benzene ring C=C).

EXAMPLE 8

In 200 ml of carbon tetrachloride, 16.6 g (0.100 mol) of 2,3,5,6-tetrafluorophenol and 13.0 g (0.125 mol) of methacrylic acid chloride were dissolved. To the resultant solution was added 20 g of molecular sieve 3 Å in diameter. The resultant mixture was stirred under reflux for 63 hours. The resultant mixture was cooled off and filtered to separate the molecular sieve. The filtrate was dried with magnesium sulfate and then rectified with a precision fractionator to recover 19.8 g of 2,3,5,6-tetrafluorophenyl methacrylate, as a fraction boiling at 56° to 57° C. (3.5 mmHg) (yield 84.6%, purity 98.5%).

The analyses obtained of the novel substance for the determination of its chemical structure were the same as those of Example 7.

EXAMPLE 9

In 40 ml of benzene, 4.1 g (0.025 mol) of 2,3,5,6-tetrafluorophenol and 3.9 g (0.0375 mol) of methacrylic acid chloride were dissolved. The resultant solution and 3.75 g (0.0375 mol) of calcium carbonate added thereto as a hydrogen chloride trapping agent were stirred under reflux for 46 hours. The reaction mixture was cooled off and filtered to separate calcium carbonate. The filtrate was rectified with a precision fractionator to recover 2.9 g of 2,3,5,6-tetrafluorophenyl methacrylate, as a fraction boiling at 56° to 57° C./3.5 mmHg.

The analyses obtained of the novel substance for the determination of its chemical structure were the same asthose of Example 7.

EXAMPLE 10

In 200 ml of carbon tetrachloride, 16.6 g (0.100 mol) of 2,3,5,6-tetrafluorophenol and 11.3 g (0.125 mol) of acrylic acid chloride were dissolved. To the resultant solution was added 20 g of molecular sieve 3 Å in diameter. The resultant mixture was stirred under reflux for 60 hours. The reaction mixture was cooled off and filtered to separate the molecular sieve. The filtrate was dried with magnesium sulfate and then rectified with a precision fractionator to recover 14.3 g of 2,3,5,6-tetrafluorophenyl acrylate, as a fraction boiling at 46° to 47° C. (3.5 mmHg) (yield 65.0%, purity 98.8%)

The analyses obtained of the novel substance for the determination of its chemical structure are shown below.

Boiling point 46°–47° C. (3.5 mmHg)
Elementary analyses

|  | C (%) | H (%) | F (%) |
| --- | --- | --- | --- |
| Calculated | 49.11 | 1.84 | 34.53 |
| Found | 49.1 | 1.86 | 34.4 |

$^1$H NMR (solvent: CCl$_4$, internal standard substance: TMS)

$\delta = 5.8$–6.7 ppm (multiplet, 3H)
$\delta = 6.95$ ppm (quintet, J$_{HF}$=9 Hz, 1H)

$^{19}$F NMR (solvent: acetone—d$_6$, external standard substance: trifluoroacetic acid)

$\delta = 64.3$ ppm (multiplet, 2F)
$\delta = 78.5$ ppm (multiplet, 2F)

Mass analysis spectrum
EI m/e=220 (M+)
Infrared absorption spectrum (neat) 1770 cm$^{-1}$ ($\nu$C=O); 1640 cm$^{-1}$ ($\nu$C=C); 1490, 1530 cm$^{-1}$ ($\nu$F— benzene ring C=C).

EXAMPLE 11

In 200 ml of methanol having 4.32 g (0.108 mol) of sodium hydroxide dissolved therein, 12 g (0.0723 mol) of 2,3,5,6-tetrafluorophenol was dissolved. The solution was kept at 0° C. with ice. To the cooled solution, 7.2 g (0.0796 mol) of acrylic acid chloride was gradually added dropwise. After completion of the dropwise addition, the mixture was stirred at the same temperature for 1.5 hours. It was combined with 160 ml of pure water and adjusted to pH 10 by addition of an aqueous 20% sodium hydroxide solution. Consequently, the reaction mixture separated into two layers. Of the two layers, the oil layer was separated, washed again with pure water, dried with anhydrous sodium sulfate, and rectified with a precision fractionator. Consequently, there was recovered 9.8 g of 2,3,5,6-tetrafluorophenyl acrylate, as a fraction boiling at 46° to 47° C./3.5 mmHg (yield 61.6 mol % based on 2,3,5,6-tetrafluorophenol).

The analyses obtained of the novel substance for the determination of its chemical structure were the same as those of Example 10.

What is claimed is:

1. A compound represented by the general formula I:

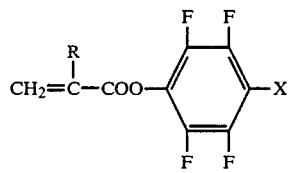

(I)

wherein R denotes hydrogen atom or methyl group and X hydrogen atom or cyano group.

2. A compound according to claim 1, wherein X is hydrogen atom.

3. A compound according to claim 2, wherein R is hydrogen atom.

4. A compound according to claim 2, wherein R is methyl group.

5. A compound according to claim 1, wherein X is cyano group.

6. A compound according to claim 5, wherein R is hydrogen atom.

7. A compond according to claim 5, wherein R is methyl group.

8. A method for the production of compounds represented by the general formula I:

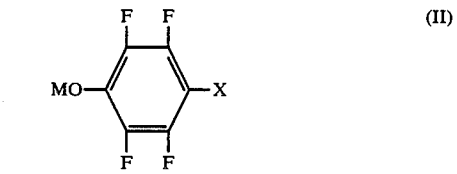

(I)

wherein R denotes hydrogen atom or methyl group and X hydrogen atom or cyano group, by the reaction of 2,3,5,6-tetrafluorophenols represented by the general formula II:

$$\text{MO} \underset{F\ F}{\overset{F\ F}{\left\langle \phantom{xxx} \right\rangle}} X \qquad (II)$$

wherein M denotes hydrogen atom or an alkali metal and X has the same meaning as described bove, with acrylic acid chloride or methacrylic acid chloride.

9. A method according to claim 8, wherein M is hydrogen atom.

10. A method according to claim 8, wherein M is an alkali metal.

11. A method according to claim 8, wherein said reaction is carried out in an organic solvent.

12. A method according to claim 8, wherein said reaction is carried out at a temperature in the range of −20° to +120° C.

13. A method according to claim 9, wherein said reaction is carried out in the presence of a hydrogen chloride trapping agent.

* * * * *